US011441550B2

(12) United States Patent
Ong

(10) Patent No.: US 11,441,550 B2
(45) Date of Patent: Sep. 13, 2022

(54) SELF-ALIGNING POWER SCREW FOR SYRINGE PUMP

(71) Applicant: Norgren Kloehn LLC, Las Vegas, NV (US)

(72) Inventor: Dickson Ong, Las Vegas, NV (US)

(73) Assignee: Norgren Kloehn LLC, Las Vegas, NV (US)

( * ) Notice: Subject to any disclaimer, the term of this patent is extended or adjusted under 35 U.S.C. 154(b) by 203 days.

(21) Appl. No.: 16/456,080

(22) Filed: Jun. 28, 2019

(65) Prior Publication Data
US 2020/0003193 A1  Jan. 2, 2020

Related U.S. Application Data

(60) Provisional application No. 62/692,346, filed on Jun. 29, 2018.

(51) Int. Cl.
| | |
|---|---|
| *F04B 9/02* | (2006.01) |
| *F04B 39/14* | (2006.01) |
| *A61M 5/145* | (2006.01) |
| *F04B 17/03* | (2006.01) |

(52) U.S. Cl.
CPC ............. *F04B 9/02* (2013.01); *A61M 5/1452* (2013.01); *F04B 17/03* (2013.01); *F04B 39/14* (2013.01); *A61M 5/1456* (2013.01)

(58) Field of Classification Search
CPC .......... F04B 9/02; F04B 39/14; F04B 53/143; F04B 17/03; A61M 5/1452; A61M 5/1456; A61M 5/20; A61M 5/14; A61M 5/142; B23P 17/02; B23P 13/02
See application file for complete search history.

(56) References Cited

U.S. PATENT DOCUMENTS

| | | | | |
|---|---|---|---|---|
| 3,897,985 | A * | 8/1975 | Davis ..................... | G01C 19/16 384/536 |
| 4,396,385 | A * | 8/1983 | Kelly .................... | A61M 5/172 604/152 |
| 4,747,828 | A * | 5/1988 | Tseo .................. | A61M 5/16854 417/20 |
| 5,176,502 | A * | 1/1993 | Sanderson .......... | A61M 5/1456 417/18 |
| 6,423,035 | B1 * | 7/2002 | Das ..................... | A61M 5/1456 128/DIG. 1 |

(Continued)

*Primary Examiner* — Essama Omgba
*Assistant Examiner* — Dnyanesh G Kasture
(74) *Attorney, Agent, or Firm* — McDonnell Boehnen Hulbert & Berghoff LLP

(57) ABSTRACT

An apparatus and method of assembling a syringe pump for accurately dispensing a fluid from a syringe. The syringe pump has a frame having a valve assembly connectable to the syringe. A linear rail is disposed in and connected to the frame, and a travel block is disposed within the frame and slidably connected to the linear rail. A connector is connected to the travel block and connectable to the syringe. A power screw having a first end rotatably supported by bearings is disposed within the frame and has a free second end opposite the first end of the power screw wherein the travel block is threadably connected to the power screw. The power screw is rotatably driven to effectively drive the travel block and the connector linearly along the linear rail thereby dispensing the fluid from the syringe.

19 Claims, 6 Drawing Sheets

(56) References Cited

U.S. PATENT DOCUMENTS

| | | | | |
|---|---|---|---|---|
| 2001/0034502 A1* | 10/2001 | Moberg | ............... | A61M 5/1456 |
| | | | | 604/67 |
| 2003/0152493 A1* | 8/2003 | Lefebvre | ................ | G01N 30/24 |
| | | | | 422/509 |
| 2005/0220639 A1* | 10/2005 | Sasaki | ................. | A61M 5/1458 |
| | | | | 417/415 |
| 2006/0078436 A1* | 4/2006 | Neeb | ....................... | F04D 5/001 |
| | | | | 417/283 |
| 2006/0184154 A1* | 8/2006 | Moberg | ............ | A61M 5/16854 |
| | | | | 604/151 |
| 2010/0129245 A1* | 5/2010 | Patel | ........................ | F04B 9/04 |
| | | | | 417/437 |
| 2010/0275705 A1* | 11/2010 | Johnson | ................. | B64G 1/283 |
| | | | | 74/5.5 |
| 2014/0377114 A1* | 12/2014 | Alaze | ................. | F04C 15/0023 |
| | | | | 418/191 |
| 2015/0157791 A1* | 6/2015 | Desch | .................. | G06F 3/0488 |
| | | | | 702/50 |
| 2015/0292495 A1* | 10/2015 | Sweeney | .................. | F04B 9/02 |
| | | | | 417/53 |
| 2017/0056581 A1* | 3/2017 | Deak | ..................... | A61M 5/172 |
| 2017/0220021 A1* | 8/2017 | Bode | ........................ | B64F 5/10 |
| 2018/0171610 A1* | 6/2018 | Ahuja | ................... | E03C 1/2302 |

\* cited by examiner

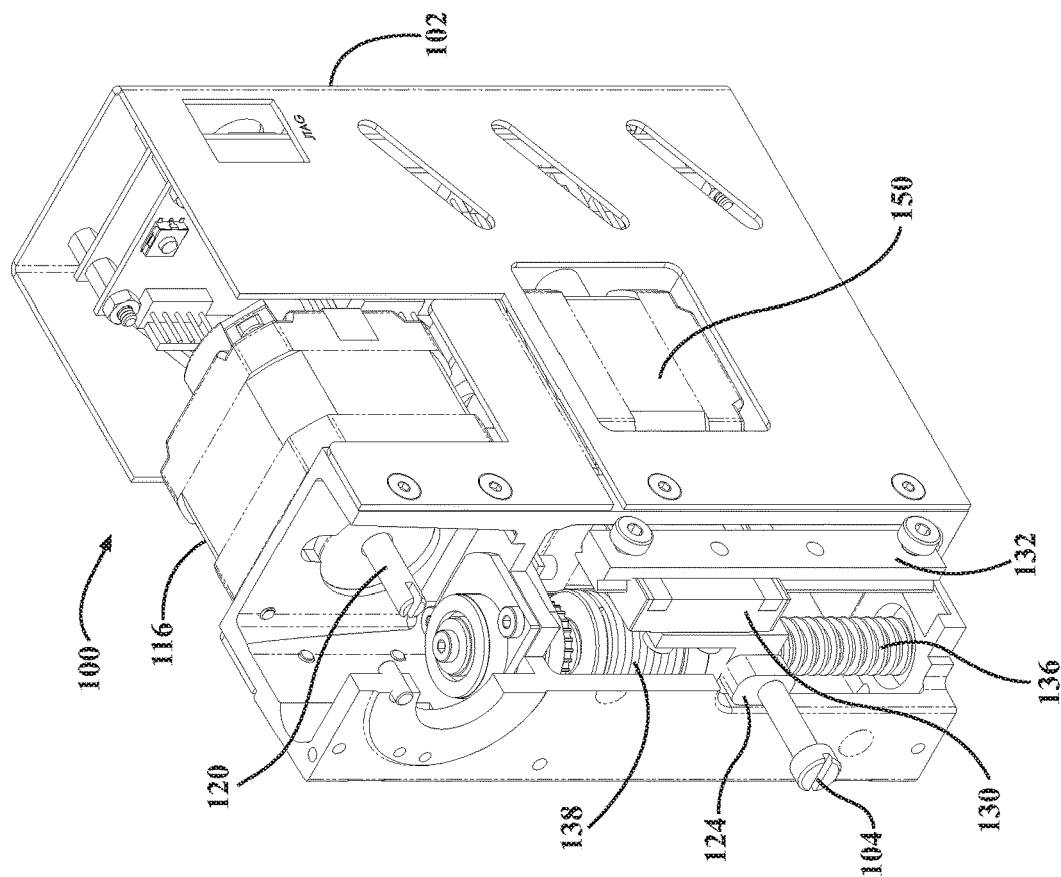
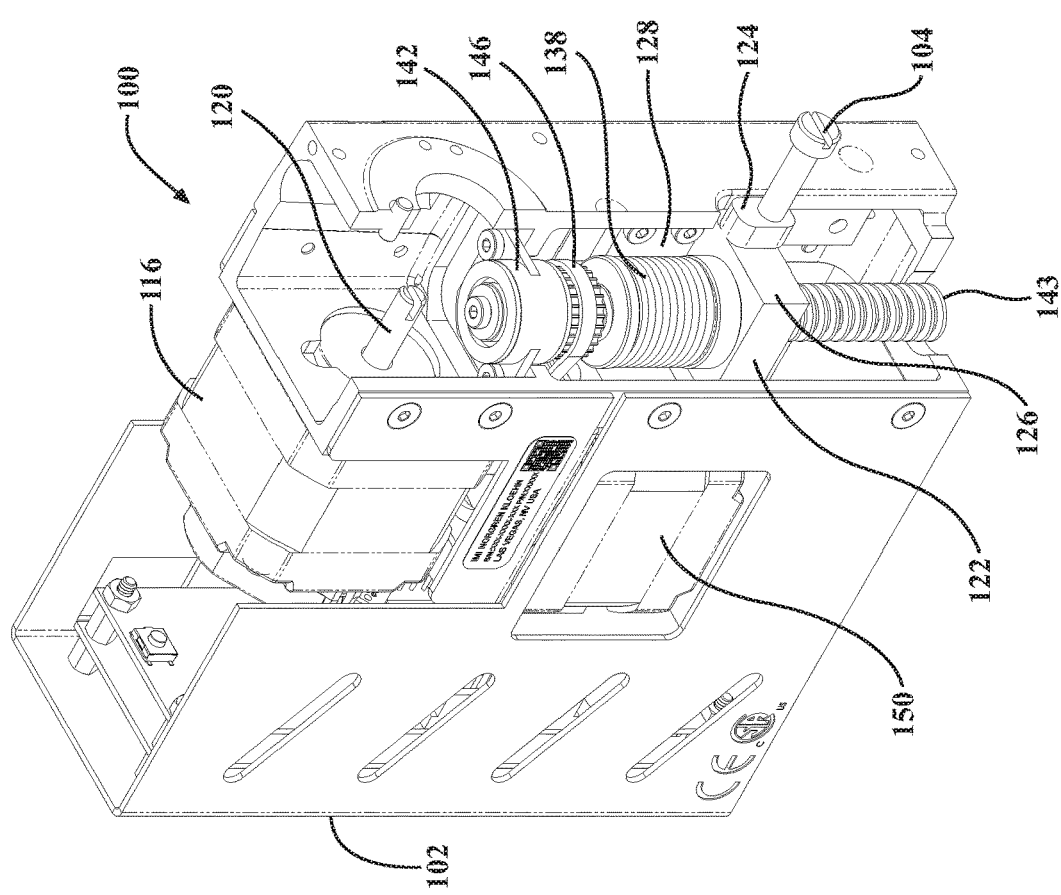

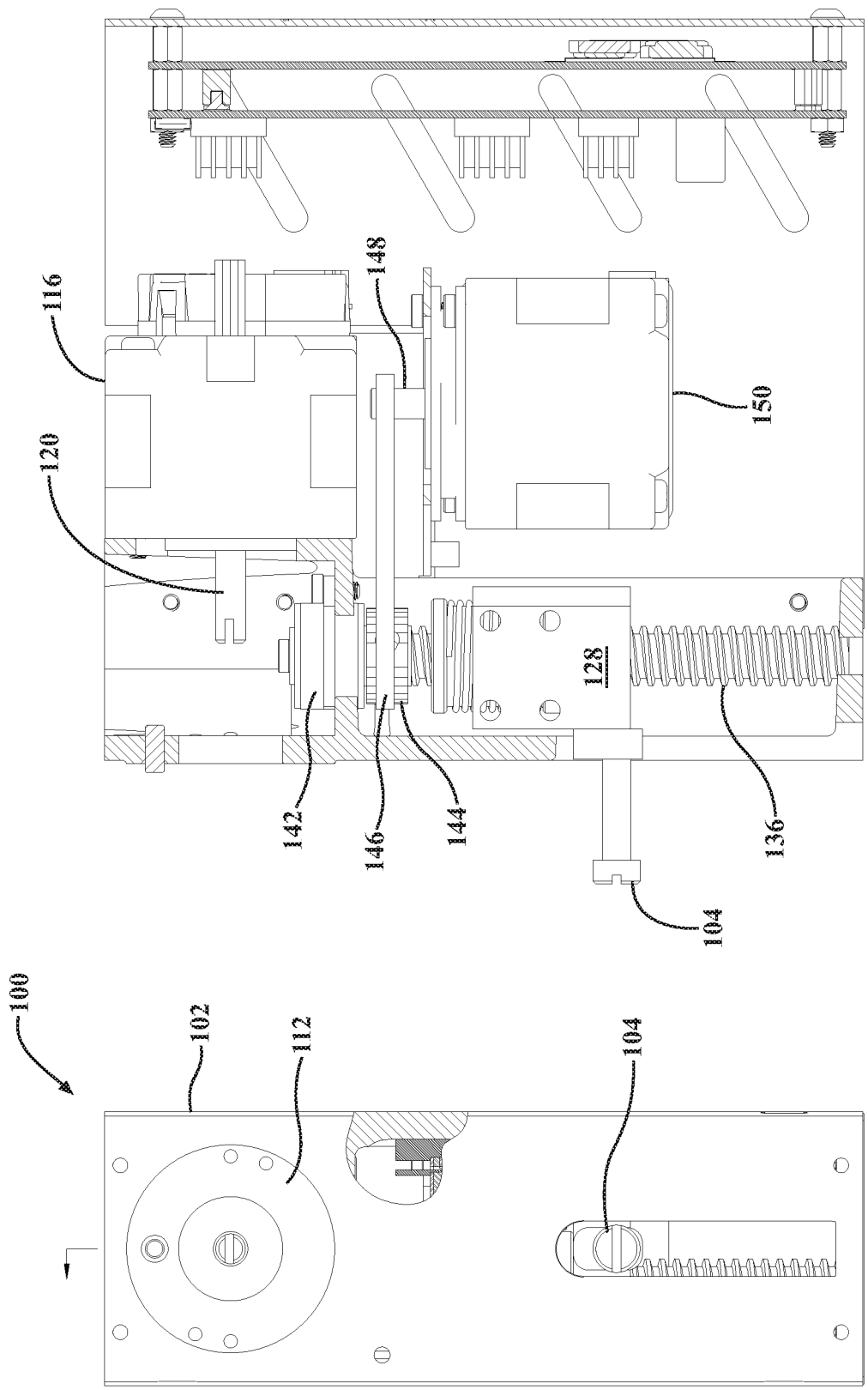

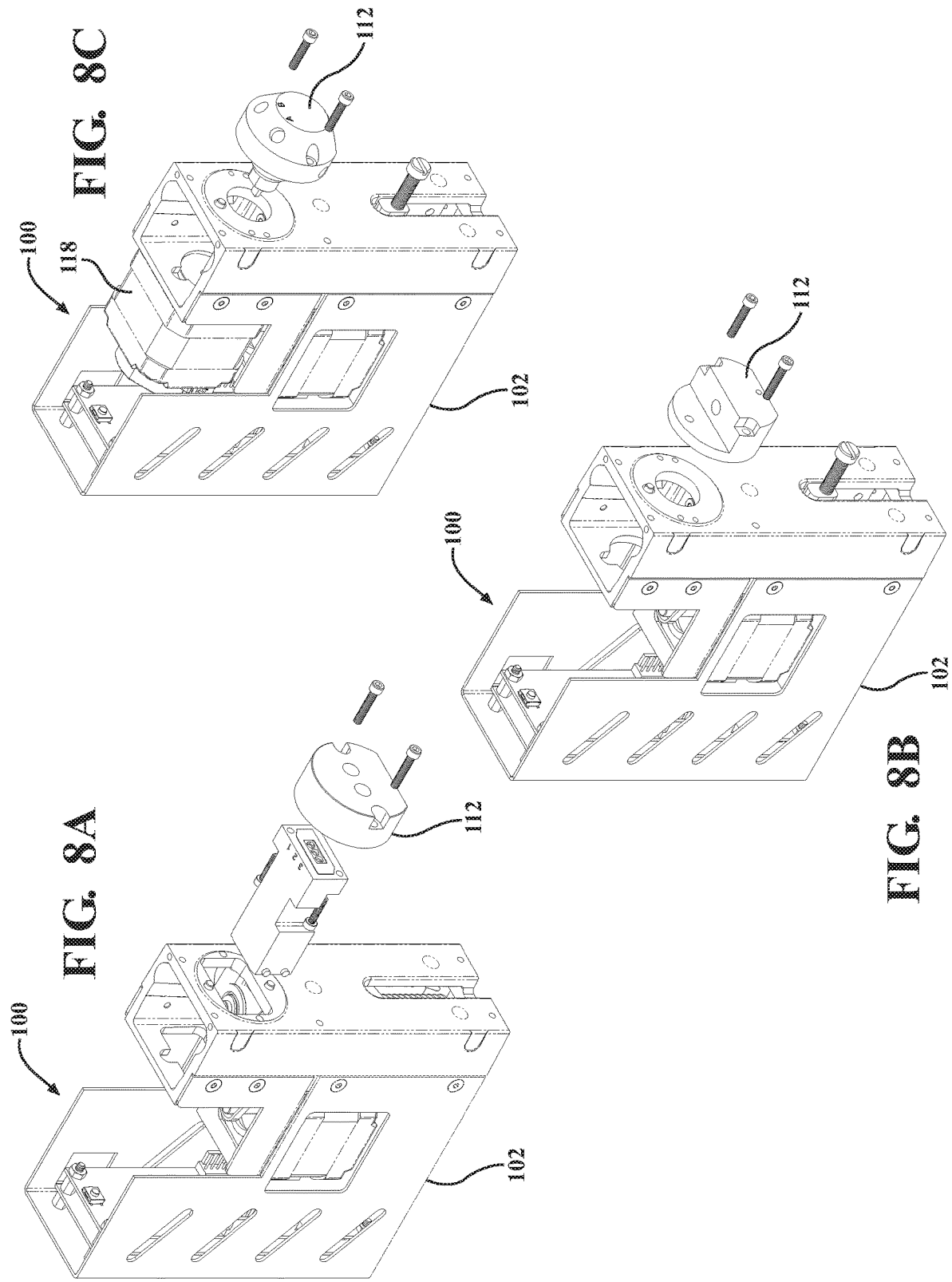

SELF-ALIGNING POWER SCREW FOR SYRINGE PUMP

CROSS-REFERENCE TO RELATED APPLICATION(S)

This application claims priority to and the benefit of U.S. Provisional Patent Application No. 62/692,346 filed on Jun. 29, 2018, the disclosure of which is incorporated herein by reference in its entirety.

TECHNICAL FIELD

The present disclosure relates to syringe pumps, and more particularly, to a syringe pump having an improved powered screw and linear rail system that enhances the precision and accuracy of the syringe pump while providing a simpler assembly process thereof.

BACKGROUND

Syringe pumps are pumps used to deliver precise and accurate amounts of fluid in various applications and industries, such as research environments, medical fields, biotechnical fields, chemical applications, etc. Such applications commonly require the delivery of small amounts of fluid which must be accurately and precisely measured. Other applications require a controlled amount of fluid over a specific time frame.

Syringe pumps are known to use a syringe comprised of a plunger sliding in a syringe tube wherein the syringe tube holds a fluid for dispensing therefrom. The plunger includes a piston-like seal that fits tightly against the inner surface of the syringe tube. Movement of the plunger may decrease the volume contained in the syringe tube between the plunger seal and an outlet of the syringe tube to provide a positive displacement pumping action which displaces the fluid from the syringe tube.

The syringe pump includes a syringe driver which provides movement of the plunger with respect to the tube via an electric motor. The motor can provide precise and slow movement of the plunger to deliver precise amounts of the fluid from the syringe tube over time without the need of a human operator. The flow rate or displacement of the fluid may be controlled by knowing the geometry of the syringe and accurately controlling the movement of the plunger.

In order to accurately control the movement of the plunger, various control systems and structures have been implemented in the syringe pump. Some syringe pumps have been known to use power screw structures to accurately drive the plunger along a linear path of movement. Other syringe pumps have been known to use linear rails or slide rails to guide or provide linear movement to the plunger, while other syringe pumps have relied on a combination of a power screw and linear rail to provide accurate linear movement of the plunger without necessarily translating rotary motion to linear motion. Although such designs are effective for controlling movement of the plunger, they are difficult and expensive to manufacture and assemble, because the accuracy and precision that is required to monitor the linear movement of the plunger requires that the power screw and/or linear rail maintain precise and accurate tolerances in both the manufacturing and the assembling of the components in the syringe pump. The difficulties and high cost of manufacturing and assembling such syringe pumps creates inefficiencies that are undesirable in an industrial environment.

The present disclosure addresses these issues by providing a syringe pump that allows for simpler manufacturing and assembly of the associated components while still providing the precision and accuracy required of the syringe pump.

SUMMARY

The present disclosure provides a syringe pump for accurately dispensing a fluid from a syringe wherein the syringe pump has a frame having a valve assembly connectable to the syringe. A linear rail is disposed in and connected to the frame, and a travel block is disposed within the frame and slidably connected to the linear rail. A connector is connected to the travel block and connectable to the syringe. A power screw having a first end rotatably supported by bearings is disposed within the frame and has a free second end opposite the first end of the power screw wherein the travel block is threadably connected to the power screw. The power screw is rotatably driven to effectively drive the travel block and the connector linearly along the linear rail thereby dispensing the fluid from the syringe. A motor driven pulley is connected to the power screw for rotatably driving the power screw.

The travel block further provides a substantially L-shaped structure having a base and a side wherein the base is substantially perpendicular to the side, and the base and side are disposed within housing. The extended portion is connected to and extends from the base and is connected to the connector. A side of the travel block is connected to a carriage, and the carriage is slidably connected to the linear rail to support linear movement of the connector.

The power screw has a stopper threadably attached to the power screw. A base of the travel block has an aperture extending therethrough for receiving and connecting the stopper to the travel block thereby allowing the travel block to travel linearly along the linear rail upon rotation of the power screw. The motor driven pulley provides a substantially cylindrical toothed pulley and a pulley belt for engaging and driving the toothed pulley. The cylindrical toothed pulley is connected to the power screw adjacent the bearings, wherein the first end of the power screw rotatably supported by the bearings is an upper end, and the free second end of the power screw is a lower end located vertically below the first end.

The valve assembly has at least one port communicable with the syringe, wherein a motor rotates the valve assembly to select and position the at least one port.

The syringe pump further provides a pair of adjoining surfaces establishing datums for enhancing the accuracy of the syringe pump. The pair of adjoining surfaces are located on the linear rail and the frame wherein the pair of adjoining surfaces are machined to establish machine datums and enhance the accuracy of the alignment between the linear rail and the frame. The pair of adjoining surfaces may also be located on the side of the travel block and the carriage wherein the pair of adjoining surfaces are machined to establish machine datums and enhance the accuracy of the alignment between the side of the travel block and the carriage.

The present disclosure also provides for a method for assembling a syringe pump that accurately dispenses fluid from a syringe while simplifying the assembly of the syringe pump. The method includes the steps of providing a frame with a valve assembly connectable to one end of the syringe; connecting a linear rail to the frame wherein the linear rail has a carriage slidably connected thereto and is disposed within the frame; connecting a travel block to the carriage; connecting a stopper, threadably attached to a power screw, to the travel block; mounting a first end of the power screw to bearings disposed within the frame; providing a motor driven pulley connected to the power screw for rotating the power screw and driving the travel block and the carriage along the power screw and the linear rail; and connecting a connector to the travel block wherein the connector is connectable to a second end of the syringe.

The method of the present disclosure may further comprise the steps of providing a pair of adjoining surfaces to establish datums for enhancing the accuracy of the syringe pump, wherein the pair of adjoining surfaces may comprise machining a machine datum surface on the frame and on the linear rail and connecting the machine datum surface of the frame to the machine datum surface of the linear rail. The pair of adjoining surfaces may also include machining a machine datum on a side of the travel block and on the carriage and connecting the machine datum surface on the side of the travel block to the machine datum surface of the carriage.

Mounting a first end of the power screw to bearings disposed within the frame may further comprise allowing the bearings to float into position to provide proper alignment of the power screw relative to the linear rail. Allowing the bearings to float into position to provide proper alignment of the power screw relative to the linear rail may also comprise allowing a second opposite end of the power screw to hang freely downward to provide proper alignment of the power screw relative to the linear rail.

BRIEF DESCRIPTION OF THE DRAWINGS

The invention is best understood from the following detailed description when read in conjunction with the accompanying drawings. It is emphasized that, according to common practice, the various features of the drawings may not be to-scale and may be arbitrarily expanded or reduced for clarity.

FIG. 4 is a left, partial break-away, isometric view of the syringe pump according to the principles of the present disclosure;

FIG. 5 is a right, partial break-away, isometric view of the syringe pump according to the principles of the present disclosure;

FIG. 6 is a front plan view and partial breakaway of the syringe pump according to the principles of the present disclosure;

FIG. 7 is a side sectional view of the syringe pump according to the principles of the present disclosure; and FIGS. 8A-8C are perspective exploded views of the valve assemblies for use in the syringe pump according to the principles of the present disclosure.

DETAILED DESCRIPTION

Figure 1:
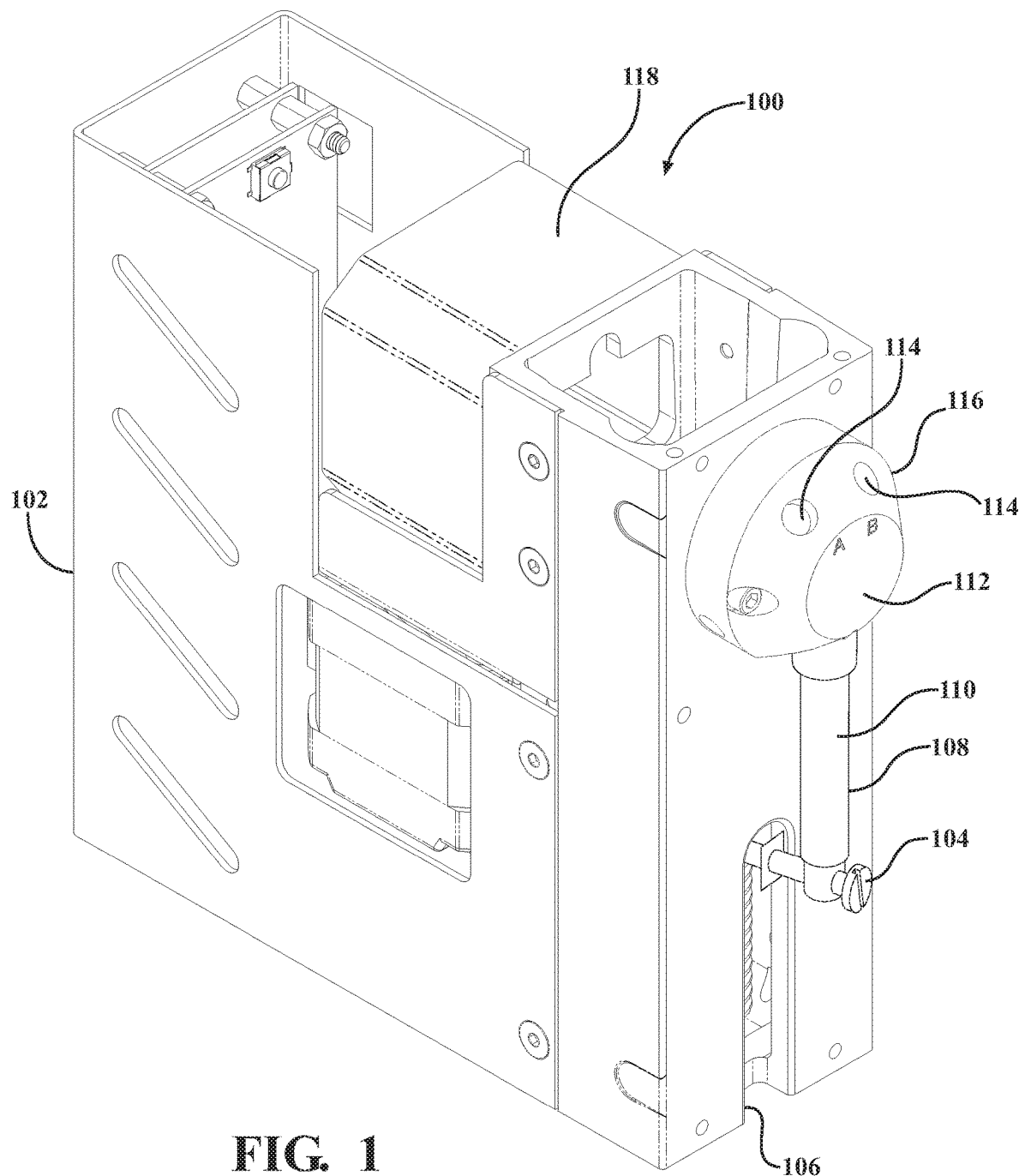
FIG. 1 is an isometric view of a syringe pump according to the principles of the present disclosure.
Figure 2:
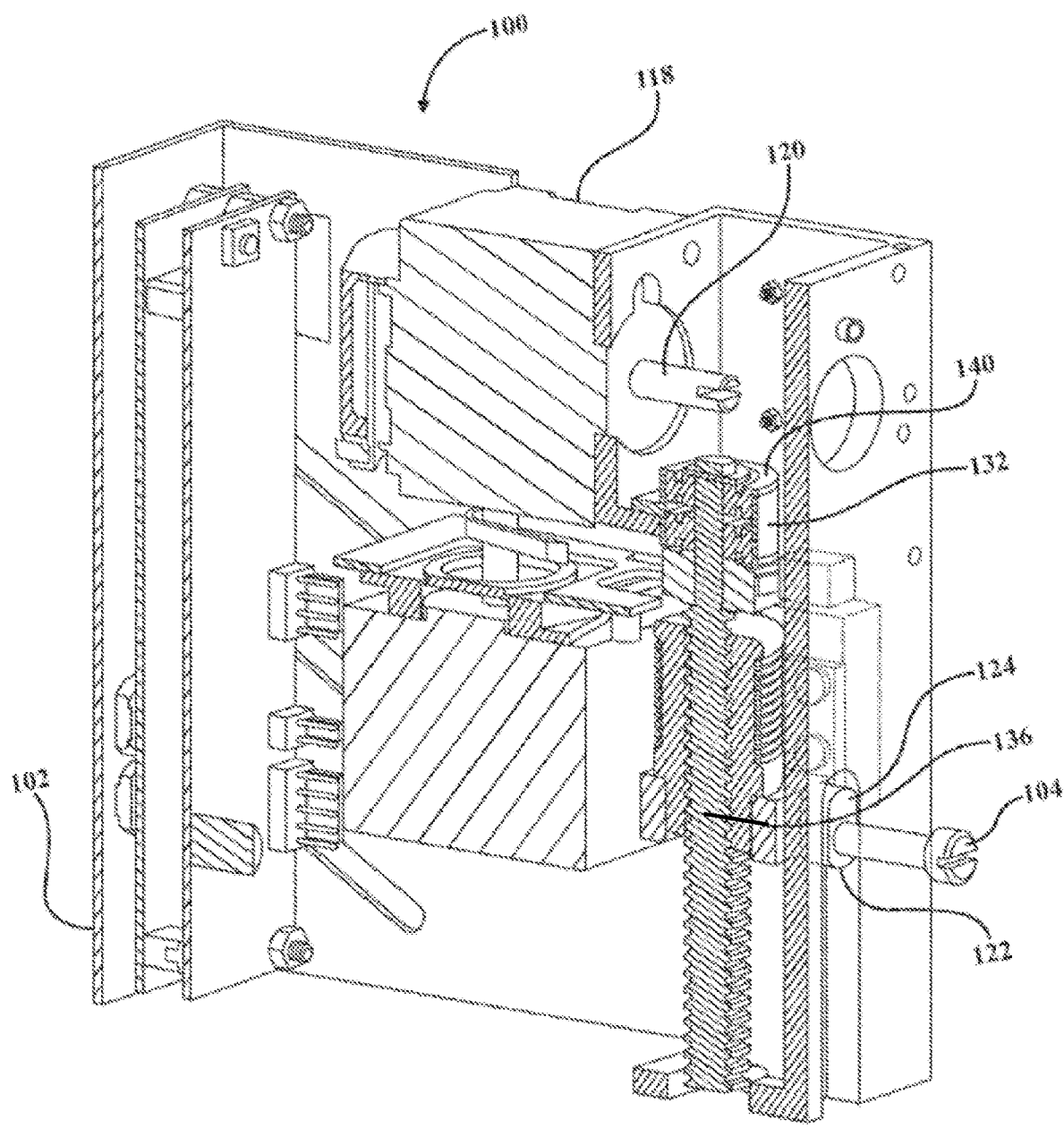
FIG. 2 is a partial break-away and sectional, isometric view of the syringe pump according to the principles of the present disclosure.
Figure 3:
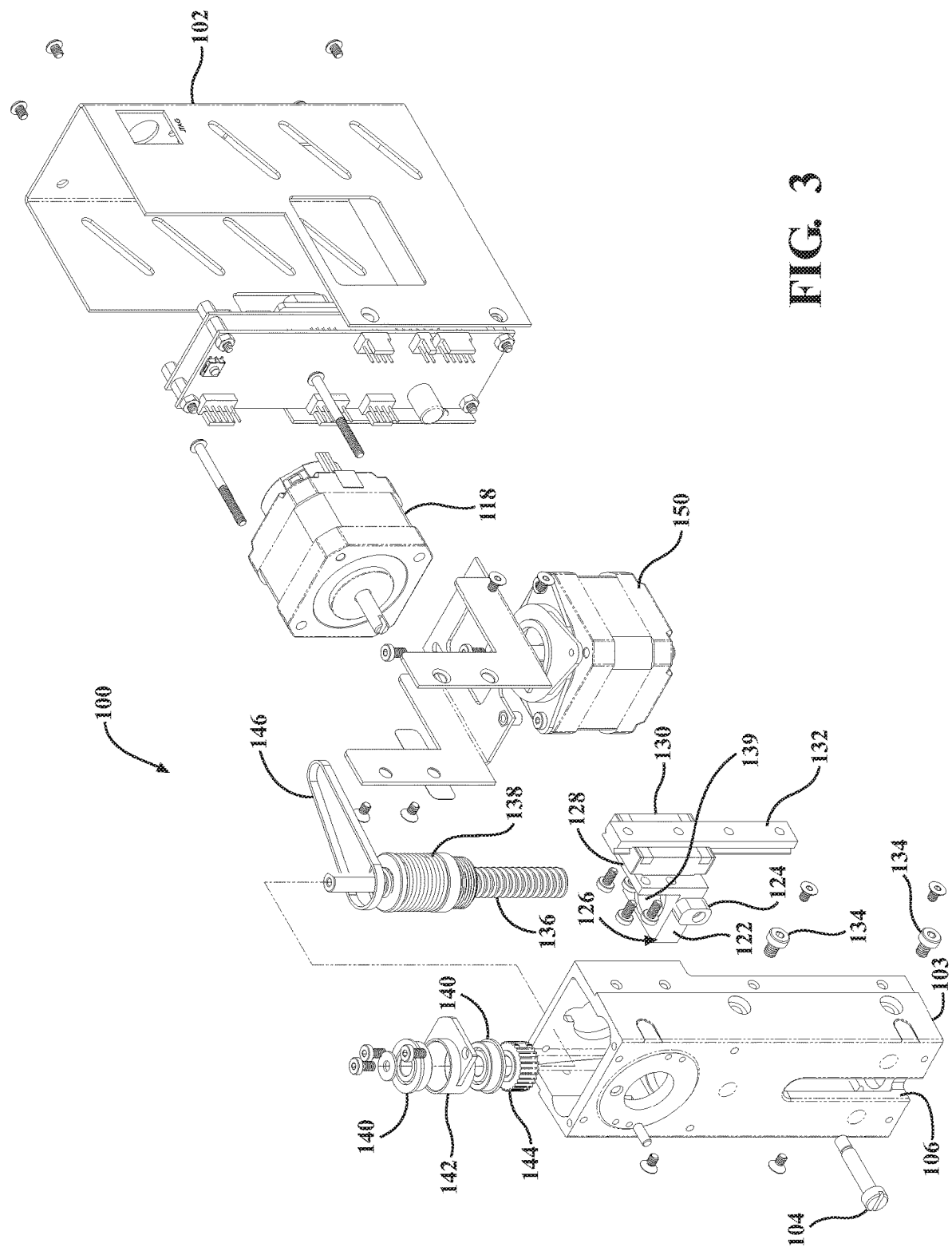
FIG. 3 is an exploded, isometric view of the syringe pump according to the principles of the present disclosure.

The present disclosure describes a syringe pump that allows for a simpler design to manufacture and assemble than previous known syringe pumps while still providing a syringe pump that accurately and precisely distributes fluid from a syringe. As seen in FIG. 1, a syringe pump 100 provides a substantially rectangular hollow housing 102 for housing certain internal components of the syringe pump 100. A substantially rectangular hollow frame 103 is connected to the housing 102 and also houses certain components of the syringe pump 100. The frame 103 further provides a slot 106 in an end wall of the frame 103, wherein a connector 104 extends through an aperture (not shown) provided in a lower end of a substantially vertically oriented syringe 108 and through the slot 106 provided in the frame 103. The connector 104 may comprise a screw, a drive pin, a snap-fit connector, or any other similar structure. The syringe 108 provides a syringe tube 110 for housing a fluid (not shown), such as a saline solution, blood, acid, chemicals, etc., wherein a plunger (not shown) is disposed within the syringe tube 110 and connected to the connector 104. The upper end of the syringe 108 is connected to a valve assembly 112 which is connected to and extends outward from the frame 103 thereby supporting and positioning the syringe 108 outside of the frame 103. The valve assembly 112 provides at least one port or aperture 114 extending through a body 116 of the valve assembly 112. An upper end of the syringe 108 is received by one of the ports 114 in the body 116 of the valve assembly 112 such that the syringe tube 110 is in communication with the selected port 114 thereby allowing the fluid to flow from the syringe tube 110 to the port 114 upon the plunger moving toward the valve assembly 112 and forcing the fluid from the syringe tube 110. Depending on the valve assembly 112, the fluid may travel through the body 116 of the valve assembly 112 to other ports 114 in the valve assembly 112, or the fluid may be directed through a single port 114. Tubing (not shown) or other communication devices may be connected to the other ports 114 in the body 116 of the valve assembly 112 to direct the flow of the fluid to predetermined destinations.

In order to adjust the position of the valve assembly 112 and select a desired port 114 to be connected to the upper end of the syringe 108, an electric motor or drive 118 may be connected to and supported by a bracket 115 connected to the frame 103 and partially disposed within the housing 102, wherein the motor 118 may be partially exposed from the housing 102, as seen in FIGS. 1-7 and 8C. A drive shaft 120 extends from the motor 118 and through an aperture provided in the frame 103, wherein the drive shaft 120 is connected to the body 116 of the valve assembly 112. Upon the motor 118 rotating the drive shaft 120, the body 116 of the valve assembly 112 may be rotated or adjusted into a position that is suitable for alignment with the syringe 108. A programmable or electronic controller (not shown) may be connected to a mounting board 121 located in and secured to the rear of the housing 102 to actuate the motor 118 and rotate the valve assembly 112 in the desired position.

As shown in FIGS. 8A-8C, numerous types of valve assemblies 112 may be utilized in the syringe pump 100. For instance, in FIG. 8A, the valve assembly 112 may have multiple ports 114 with valves (not shown) that are actuated by a solenoid 123 thereby not requiring the motor 118 shown in FIGS. 1 and 8C. In FIG. 8B, the valve assembly 112 may only have one port 114 thereby not requiring rotation of the valve assembly 112 and thus, not requiring the motor 118 shown in FIGS. 1 and 8C. In FIG. 8C, the valve assembly 112 has multiple ports 114 and may be rotated by the motor 118 to a desired position. The disclosure shown in FIG. 8C is the disclosure represented in FIGS. 1-7 and fully described in the specification.

To precisely move the connector 104 for the purpose of accurately dispersing the fluid from the syringe 108, the connector 104 is connected to a travel block 122 located within the frame 103, wherein an extended portion 124 of the travel block 122 receives the connector 104, and the slot 106 provided in the frame 103 provides clearance to allow the extended portion 124 to travel linearly within the slot 106 while not engaging the walls defining the slot 106, as shown in FIGS. 2-7. The travel block 122 further provides a substantially L-shaped structure having a base 126 that is substantially perpendicular to a side 128 wherein the base 126 and the side 128 are disposed within the frame 103. The extended portion 124 is connected to and extends from the base 126 into the slot 106 of the housing 102.

In order to support linear movement of the connector 104, the side 128 of the travel block 122 is connected to a carriage 130, wherein the carriage 130 is slidably connected to a linear rail 132 disposed within the frame 103. The linear rail 132 is connected to an inside wall of the frame 103 by conventional fasteners 134. The linear rail 132 is designed for the purpose of handling heavy loads and achieving precise alignment and movement along the linear rail 132. To assist in the alignment of the linear rail 132 to the frame 103, machined datums are used for assembly by machining an edge or surface within the housing 102 and on the linear rail 132 so as to mount the adjoining surfaces thereto. In addition, the side 128 of the travel block 122 and the carriage 130 are also machined to provide a machine datum surface that allows for alignment of the travel block 122 to the carriage 130. The sliding engagement of the carriage 130 on the linear rail 132 also are machined to provide a machine datum surface for proper alignment of the carriage 130 and the linear rail 132. It is anticipated that other linear guides, such as linear guide rods, could be used in place of the linear rail 132.

To drive the travel block 122 along the linear rail 132, the syringe pump 100 provides a power screw 136 having a stopper 138 threadably attached to the power screw 136 for linear travel of the stopper 138 upon rotation of the power screw 136, wherein the power screw 136 and the stopper 138 are disposed within the frame 103. The power screw 136 may comprise a ball screw, lead screw, or other similar structure. The base 126 of the travel block 122 provides an aperture 139 extending therethrough, wherein the stopper 138 is received by the aperture 139 and connected to the travel block 122 thereby allowing the travel block 122 to travel linearly along the linear rail 132 with the carriage 130 upon rotation of the power screw 136. An upper end of the power screw 136 may be rotatably supported by a pair of bearings 140 housed within a fixed bearing housing 142 which is disposed within the frame 103 of the syringe pump 100. An opposite or lower end of the power screw 136 extends freely downward and is allowed to float within an aperture provided in a bottom wall of the frame 103 without being supported by or connected to a structure. To drive the power screw 136, a cylindrical toothed pulley 144 is fixedly connected to the power screw 136 just below the bearings 140 in the bearing housing 142. A pulley belt 146 extends around the toothed pulley 144 and a drive shaft 148 of an electric motor or drive 150, wherein the electric motor 150 is mounted to the bracket 115 below the motor 118 and within the housing 102. The electric motor 150 drives the pulley belt 146 so as to rotate the power screw 136 thereby driving the stopper 138 and the travel block 122 along the power screw 136 and the linear rail 132. It should be noted that the present disclosure is not limited to a motor driven pulley, but rather, any type of drive is anticipated, including but not limited to, direct drives, gear assemblies, etc. An electronic or programmable controller (not shown) may be connected to the mounting board 121 and utilized to control the rotation of the electric motor 150.

When assembling the syringe pump 100, the linear rail 132 is first located and connected to the frame 103 via the machined surfaces, and the side 128 of the travel block 122 is connected to the carriage 130 via the machined surfaces, wherein the carriage 130 slidably engages the linear rail 132. The power screw 136 and the stopper 138 are then connected to the travel block 122. By using the appropriate machine datums on the travel block 122, the carriage 130, the linear rail 132, and the frame 103, the travel axis of the power screw 136 is ensured to be substantially parallel to the travel axis of the linear rail 132. Once the above noted components are secured to the frame 103, the bearings 140 and the bearing housing 142 are allowed to float into their final position. This alleviates any chances for binding and ensures that the components related to driving the connector 104 are in alignment thereby eliminating complex and expensive assembly processes regarding alignment. The free bottom end 143 of the power screw 136 allows and prohibits the design from being affected by component tolerance stack ups thereby allowing for more relaxed tolerances on each individual component which in turn reduces manufacturing costs. By ensuring the proper alignment of the associated components, the syringe pump 100 consistently achieves high linear precision and accuracy through a relatively simple assembly process.

Persons skilled in the art will understand that the various embodiments of the disclosure described herein and shown in the accompanying figures constitute non-limiting examples, and that additional components and features may be added to any of the embodiments discussed hereinabove without departing from the scope of the present disclosure. Additionally, persons skilled in the art will understand that the elements and features shown or described in connection with one embodiment may be combined with those of another embodiment without departing from the scope of the present disclosure and will appreciate further features and advantages of the presently disclosed subject matter based on the description provided. Variations, combinations, and/or modifications to any of the embodiments and/or features of the embodiments described herein that are within the abilities of a person having ordinary skill in the art are also within the scope of the disclosure, as are alternative embodiments that may result from combining, integrating, and/or omitting features from any of the disclosed embodiments.

Use of the term "optionally" with respect to any element of a claim means that the element may be included or omitted, with both alternatives being within the scope of the claim. Additionally, use of broader terms such as "comprises," "includes," and "having" should be understood to provide support for narrower terms such as "consisting of," "consisting essentially of," and "comprised substantially of." Accordingly, the scope of protection is not limited by the description set out above, but is defined by the claims that follow, and includes all equivalents of the subject matter of the claims.

In the preceding description, reference may be made to the spatial relationship between the various structures illustrated in the accompanying drawings, and to the spatial orientation of the structures. However, as will be recognized by those skilled in the art after a complete reading of this disclosure, the structures described herein may be positioned and oriented in any manner suitable for their intended purpose. Thus, the use of terms such as "above," "below," "upper," "lower," "inner," "outer," "upward," "downward," "inward," "outward," etc., should be understood to describe a relative relationship between structures and/or a spatial orientation of the structures. Those skilled in the art will also recognize that the use of such terms may be provided in the context of the illustrations provided by the corresponding figure(s).

Additionally, terms such as "approximately," "generally," "substantially," and the like should be understood to allow for variations in any numerical range or concept with which they are associated. For example, it is intended that the use of terms such as "approximately" and "generally" should be understood to encompass variations on the order of 25%, or to allow for manufacturing tolerances and/or deviations in design.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

The invention claimed is:

1. A syringe pump for accurately dispensing a fluid from a syringe, comprising:
    a frame having a valve assembly connectable to the syringe;
    a linear rail disposed in and connected to the frame;
    a travel block disposed within the frame and slidably connected to the linear rail;
    a connector connected to the travel block and connectable to the syringe;
    a power screw having a first end rotatably supported by a floating arrangement of bearings disposed within the frame and a free second end opposite the first end of the power screw, such that the free second end is allowed to move relative to the first end supported by the floating arrangement of bearings to allow the power screw to be aligned relative to the linear rail, wherein the travel block is threadably connected to the power screw, and wherein the floating arrangement of bearings comprises: (i) a fixed bearing housing disposed within the frame about the first end of the power screw, (ii) a first bearing housed within the fixed bearing housing, and (iii) a second bearing housed within the fixed bearing housing axially-apart from the first bearing along a longitudinal axis of the power screw; and
    the power screw being rotatably driven to effectively drive the travel block and the connector linearly along the linear rail thereby dispensing the fluid from the syringe.

2. The syringe pump stated in claim 1, further comprising:
    a motor driven pulley connected to the power screw for rotatably driving the power screw.

3. The syringe pump as stated in claim 2, wherein the motor driven pulley provides a substantially cylindrical toothed pulley and a pulley belt for engaging and driving the toothed pulley.

4. The syringe pump as stated in claim 3, wherein the cylindrical toothed pulley is connected to the power screw adjacent the bearings.

5. The syringe pump as stated in claim 1, wherein the travel block further provides a substantially L-shaped structure having a base and a side wherein the base is substantially perpendicular to the side, and the base and side are disposed within housing.

6. The syringe pump as stated in claim 5, wherein an extended portion is connected to and extends from the base and is connected to the connector.

7. The syringe pump as stated in claim 1, wherein a side of the travel block is connected to a carriage, and the carriage is slidably connected to the linear rail to support linear movement of the connector.

8. The syringe pump as stated in claim 1, wherein the power screw has a stopper mounted about and threadably attached to the power screw, such that the stopper radially surrounds the power screw and the power screw extends through the stopper.

9. The syringe pump as stated in claim 8, wherein a base of the travel block has an aperture extending axially therethrough such that both the power screw and the stopper are axially received by the aperture, and connecting the stopper to the travel block thereby allowing the travel block to travel linearly along the linear rail upon rotation of the power screw.

10. The syringe pump as stated in claim 8, wherein a pair of adjoining surfaces establish datums for enhancing the accuracy of the syringe pump.

11. The syringe pump as stated in claim 10, wherein the pair of adjoining surfaces are located on the linear rail and the frame wherein the pair of adjoining surfaces are machined to establish machine datums and enhance the accuracy of the alignment between the linear rail and the frame.

12. The syringe pump as stated in claim 10, wherein the pair of adjoining surfaces are located on the side of the travel block and a carriage wherein the pair of adjoining surfaces are machined to establish machine datums and enhance the accuracy of the alignment between the side of the travel block and the carriage.

13. The syringe pump as stated in claim 1, wherein the first end of the power screw rotatably supported by the floating arrangement of bearings is an upper end, and the free second end of the power screw is a lower end located vertically below the first end.

14. The syringe pump as stated in claim 1, wherein the valve assembly has at least one port communicable with the syringe.

15. The syringe pump as stated in claim 14, further comprising:
    a first motor having a first output shaft configured to drive the power screw; and
    a second motor having a second output shaft configured to rotate the valve assembly to select and position the at least one port, and wherein the first output shaft is perpendicular to the second output shaft.

16. A method for assembling a syringe pump that accurately dispenses fluid from a syringe while simplifying the assembly of the syringe pump, comprising the steps of:
    providing a frame with a valve assembly connectable to one end of the syringe;
    connecting a linear rail to the frame wherein the linear rail has a carriage slidably connected thereto and is disposed within the frame;
    connecting a travel block to the carriage;
    connecting a stopper, threadably attached to a power screw, to the travel block;
    mounting a first end of the power screw to a floating arrangement of bearings disposed within the frame and comprising: (i) a fixed bearing housing disposed within the frame about the first end of the power screw, (ii) a first bearing housed within the fixed bearing housing, (iii) and a second bearing housed within the fixed bearing housing axially-apart from the first bearing along a longitudinal axis of the power screw, wherein mounting the first end of the power screw to the floating arrangement of bearings comprises allowing the first bearing and the second bearing to float into position to allow a second opposite end of the power screw to hang freely and move relative to the first end to provide proper alignment of the power screw relative to the linear rail;

providing a motor driven pulley connected to the power screw for rotating the power screw and driving the travel block and the carriage along the power screw and the linear rail; and connecting a connector to the travel block wherein the connector is connectable to a second end of the syringe.

17. The method of claim 16, further comprising the steps of:

providing a pair of adjoining surfaces establish datums for enhancing the accuracy of the syringe pump.

18. The method of claim 17, wherein providing the pair of adjoining surfaces further comprises the steps of:

machining a machine datum surface on the frame and on the linear rail; and connecting the machine datum surface of the frame to the machine datum surface of the linear rail.

19. The method of claim 17, wherein providing the pair of adjoining surfaces further comprises the steps of:

machining a machine datum on a side of the travel block and on the carriage; and connecting the machine datum surface on the side of the travel block to the machine datum surface of the carriage.

* * * * *